(12) United States Patent
Weber et al.

(10) Patent No.: US 9,681,938 B2
(45) Date of Patent: Jun. 20, 2017

(54) DEVICES FOR OBSTRUCTING PASSAGE OF AIR OR OTHER CONTAMINANTS INTO A PORTION OF A LUNG AND METHODS OF USE

(71) Applicant: BOSTON SCIENTIFIC SCIMED, INC., Maple Grove, MN (US)

(72) Inventors: Jan Weber, Maastricht (NL); Aiden Flanagan, Kilcolgan (IE); Torsten Scheuermann, Munich (DE)

(73) Assignee: Boston Scientific Scimed, Inc., Maple Grove, MN (US)

(*) Notice: Subject to any disclaimer, the term of this patent is extended or adjusted under 35 U.S.C. 154(b) by 426 days.

(21) Appl. No.: 14/229,302

(22) Filed: Mar. 28, 2014

(65) Prior Publication Data
US 2014/0324094 A1 Oct. 30, 2014

Related U.S. Application Data

(60) Provisional application No. 61/816,568, filed on Apr. 26, 2013.

(51) Int. Cl.
*A61F 2/00* (2006.01)
*A61F 2/04* (2013.01)
(Continued)

(52) U.S. Cl.
CPC .......... *A61F 2/04* (2013.01); *A61B 17/12104* (2013.01); *A61F 2/86* (2013.01); *A61B 5/0816* (2013.01); *A61B 17/1204* (2013.01); *A61B 17/12036* (2013.01); *A61B 17/12177* (2013.01); *A61B 2017/00221* (2013.01); *A61B 2017/00411* (2013.01); *A61B 2017/00699* (2013.01);
(Continued)

(58) Field of Classification Search
CPC .. A61F 2/04; A61M 16/0406; A61M 16/0468
USPC ....................... 128/207.16, 205.24
See application file for complete search history.

(56) References Cited

U.S. PATENT DOCUMENTS

| 7,371,223 B2* | 5/2008 | Couvillon, Jr. ..... F04B 43/0054 600/16 |
| 2008/0072914 A1* | 3/2008 | Hendricksen .... A61B 17/12022 128/207.16 |

(Continued)

FOREIGN PATENT DOCUMENTS

| WO | WO 03/041779 A1 | 5/2003 |
| WO | WO 2008/112797 A2 | 9/2008 |
| WO | WO 2013/040198 A2 | 3/2013 |

OTHER PUBLICATIONS

International Search Report and Written Opinion issued in corresponding International Application No. PCT/US2014/032222, mailed Oct. 27, 2014 (16 pages).

(Continued)

*Primary Examiner* — Thomas J Sweet
*Assistant Examiner* — Wade P Schutte
(74) *Attorney, Agent, or Firm* — Bookoff McAndrews, PLLC

(57) ABSTRACT

Provided are devices, systems and methods of selectively controlling air flow into one or more section of a patient's lungs. In particular, the devices may be valve devices having an inner lumen configured to transition between a first diameter and a second diameter smaller than the first diameter to control the airflow through the valve.

19 Claims, 7 Drawing Sheets

(51) Int. Cl.
*A61F 2/86* (2013.01)
*A61F 2/48* (2006.01)
*A61B 17/12* (2006.01)
*A61B 17/00* (2006.01)
*A61B 5/08* (2006.01)
*A61B 90/00* (2016.01)

(52) U.S. Cl.
CPC ............... *A61B 2017/00734* (2013.01); *A61B 2017/00809* (2013.01); *A61B 2017/00867* (2013.01); *A61B 2017/00876* (2013.01); *A61B 2017/1205* (2013.01); *A61B 2090/3966* (2016.02); *A61F 2002/043* (2013.01); *A61F 2002/482* (2013.01)

(56) References Cited

U.S. PATENT DOCUMENTS

| | | | | |
|---|---|---|---|---|
| 2008/0262341 A1* | 10/2008 | Boyden | ...................... | A61F 2/02 600/424 |
| 2009/0107494 A1* | 4/2009 | Freitag | .................. | A61M 16/00 128/203.12 |
| 2011/0226238 A1 | 9/2011 | Barrett et al. | | |
| 2014/0031951 A1* | 1/2014 | Costello | ................... | A61F 2/24 623/23.68 |

OTHER PUBLICATIONS

Invitation to Pay Additional Fees and, Where Applicable, Protest Fee issued in corresponding International Application No. PCT/US2014/032222, mailed Aug. 25, 2014 (6 pages).

* cited by examiner

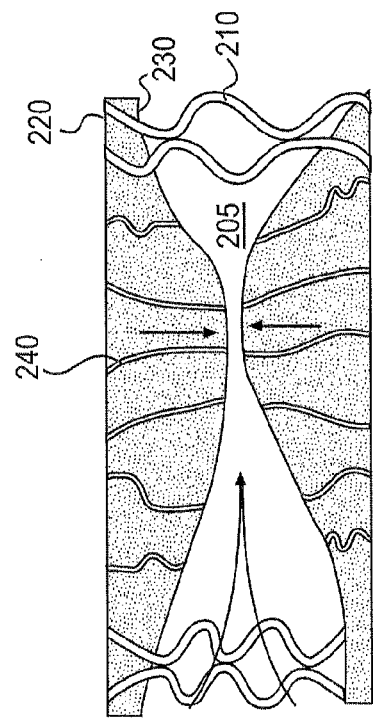
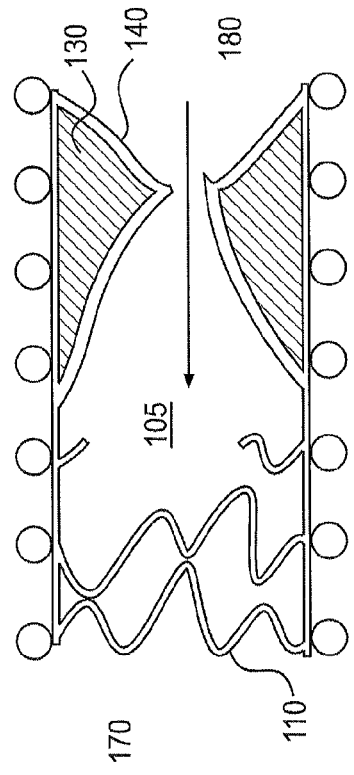
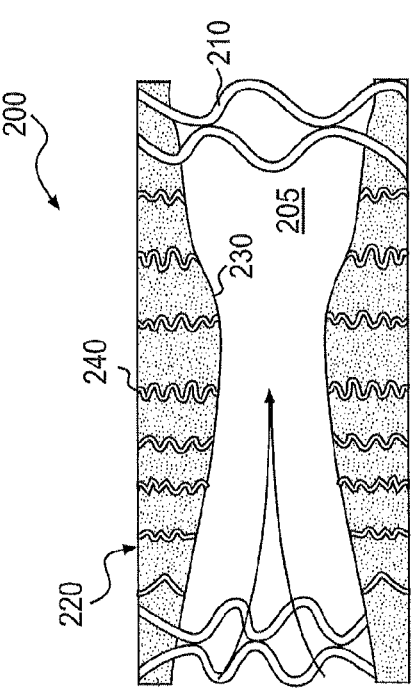
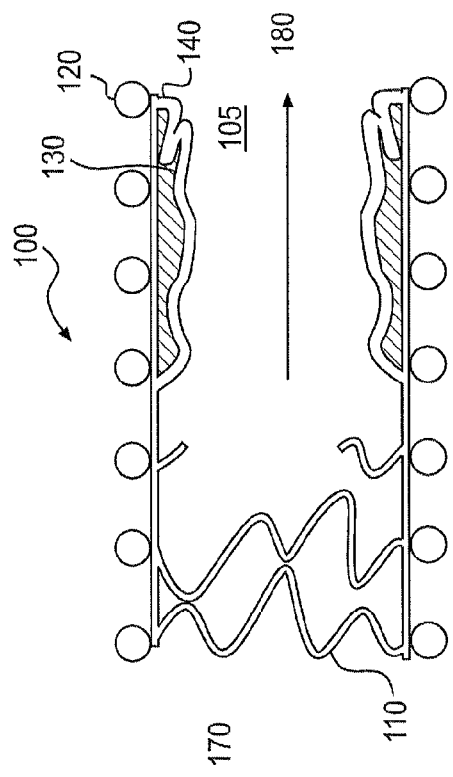

DEVICES FOR OBSTRUCTING PASSAGE OF AIR OR OTHER CONTAMINANTS INTO A PORTION OF A LUNG AND METHODS OF USE

CROSS-REFERENCE TO RELATED APPLICATIONS

This application claims the benefit of priority from U.S. Provisional Application No. 61/816,568, filed on Apr. 26, 2013, the entirety of which is incorporated by reference herein.

FIELD

Embodiments of the disclosure relate generally to medical devices and methods of treating medical conditions. In particular, embodiments of the present disclosure relate to medical devices having a valve. More specifically, embodiments of the present disclosure relate to medical devices having a valve which may selectively control air flow into sections of one or more lungs of a patient.

BACKGROUND

Chronic obstructive pulmonary disease (COPD) is a disease of the lungs in which the airways narrow over time limiting airflow into and out of the lungs causing shortness of breath. In most cases, advanced stages of COPD may lead to breathing difficulties caused by the inability of the lungs to inflate/deflate due to severe air trapping. One type of COPD is emphysema in which the airways distal to the terminal non-respiratory bronchioles enlarge due to the breakdown and destruction of the alveolar walls. Emphysema can result in air trapping, hyperinflation, and dynamic hyperinflation, each of which may reduce a patient's ability to respire. This reduction in a patient's ability to respire may ultimately lead to respiratory failure. In essence, in emphysema patients, the residual volume of the airways distal to the terminal non-respiratory bronchioles increases significantly, leaving little remaining room in their thoracic cage to breath.

COPD is most commonly caused by noxious particles or gas, often from tobacco smoking, which triggers an abnormal inflammatory response in the lung and which may damage or destroy lung tissue. Conventionally, Lung Volume Reduction Surgery (LVRS) has been used to remove diseased and/or emphysematous lung tissue, thereby allowing the expansion of the remaining (e.g. healthier) portions of the lung tissue. This procedure is possible because the lungs are divided up into relatively independent functional units. Specifically, the lungs are divided up by fissures into a predictable arrangement of lobes. For example, a human right lung includes three lobes—a superior lobe, a middle lobe, and an inferior lobe. A human left lung includes two lobes—a superior lobe and an inferior lobe. The lobes are characterized by a discrete connection with the first subdivision of the bronchial tree after the level of the principal bronchi to both lungs—the lobar bronchi. In a similar manner, the vascular, nerve, and lymphatic supply from the hila to each lobe has minimal connection with other lobes. This makes the lobes relatively independent functional units within the lung. Indeed, pathology may be confined to one lobe and corrective surgery may be facilitated by the clear demarcation between lobes produced by the fissures.

Contrary to intuition, LVRS has been shown to help improve breathing ability, lung capacity and overall quality of life. The healthy alveoli are able to inflate more fully and dead space is reduced. LVRS, however, may cause extensive discomfort to patients, and may pose serious health risks due to the invasive nature of the procedure. Lung transplantation is another surgical treatment for homogeneous (diffuse) emphysema. However, lung transplantation suffers from similar drawbacks as LVRS and may be an unrealistic option for most patients as lung transplant eligibility is limited both by stringent patient selection criteria and the scarcity of donor lungs.

Therefore, a need exists for a minimally invasive treatment that selectively controls air flow into the lungs to allow expansion of healthier portions of the lungs.

SUMMARY

Embodiments of the present disclosure relate to a devices for selectively controlling air flow.

In accordance with an aspect of the present disclosure, a device for selectively controlling air flow may include an elongate member having a proximal end, a distal end, and a lumen extending therebetween; an inner member disposed about a portion of the lumen, the inner member may be configured to transition between a first configuration and a second configuration, in the first configuration, the portion of the lumen including the inner member may define a first diameter, and, in the second configuration, the portion of the lumen including the inner member may define a second diameter smaller than the first diameter; and an actuation member for transitioning the inner member between the first configuration and the second configuration.

Various embodiments of the device may include one or more of the following features: the elongate member may include a wire frame having a plurality of interconnected wires, the wire frame may include an outer cover disposed about a portion of the wire frame, the actuation member may be configured to transition the inner member from the first configuration to the second configuration in response to a magnetic force, the actuation member may include an electro-active polymer disposed on the inner member, the electro-active polymer may be connected to an electrical power source, the actuation member may be configured to transition the inner member from the first configuration to the second configuration in response to a stimulus, the inner member may be biased in one of the first or second configurations.

In accordance with another aspect, is a system for controlling air flow in parts of a lung that may include a plurality of valve devices; and a controller coupled to the plurality of valve devices configured to control power supplied to the plurality of valve devices, each of the plurality of valve devices may include an elongate member having a proximal end, a distal end, and a lumen extending therebetween, an inner member disposed about a portion of the lumen, the inner member may be configured to transition between a first configuration and a second configuration, in the first configuration, the portion of the lumen including the inner member may define a first diameter, and in the second configuration, the portion of the lumen including the inner member may define a second diameter smaller than the first diameter, and may include an actuation member for transitioning the inner member between the first configuration and the second configuration, the actuation member may be disposed on a portion of the inner membrane.

Various embodiments of system may include one or more of the following features; the elongate member may include a wire frame, the actuation member may include a plurality of magnets, the wire frame may include an outer cover disposed about a portion of the wire frame, the actuation member may include an electro-active member disposed on the inner member, the electro-active polymer may be deposited in one or more parallel stripes, the actuation may be configured to transition the inner member from the first configuration to the second configuration, the inner member may be biased in one of the first or second configurations.

Another aspect of the present disclosure includes a method of controlling air flow in a patient, and may include steps of implanting a plurality of valve devices in a lung, in which each of the plurality of valve devices may include an elongate member having a proximal end, a distal end, and a lumen extending therebetween, an inner member disposed about a portion of the lumen, in which the inner member is configured to transition between a first configuration and a second configuration, in the first configuration, the portion of the lumen including the inner member may define a first diameter, and in the second configuration, the portion of the lumen including the inner member may define a second diameter smaller than the first diameter, and an actuation member that may transition the inner member between the first configuration and the second configuration; and actuating the actuation member to transition the inner member from the first configuration to the second configuration so as to reduce a dimension of the lumen.

Various embodiments of the method may include one or more of the following features: the elongate member may include a wire frame, the actuation member may include a plurality of magnets, providing a magnetic force to actuate the actuating member and transition the inner member from the first configuration to the second configuration.

Additional objects and advantages of the present disclosure will be set forth in part in the description which follows, and in part will be obvious from the description, or may be learned by practice of the claimed invention. The objects and advantages of the claimed invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIGS. 1A and 1B are side views of an implanted valve device, according to an embodiment of the present disclosure, showing relaxed and contracted positions of the valve device.

FIGS. 2A and 2B are side views of an implanted valve device, according to another embodiment of the present disclosure, showing relaxed and contracted positions of the valve device.

DESCRIPTION OF THE EMBODIMENTS

Figure 3B:
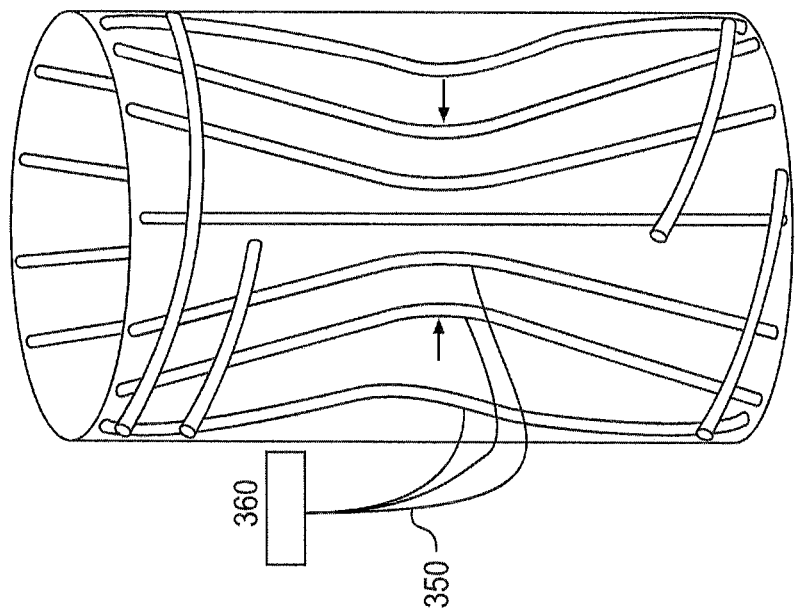
FIGS. 3A and 3B are perspective views of a valve device, according to another embodiment of the present disclosure.

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device in a patient. By contrast, "proximal" refers to the end closest to the medical professional when placing a device in the patient.

Overview

Embodiments of the present disclosure relate to devices, systems, and methods for controlling air flow. In particular, embodiments of the present disclosure relate to devices, systems, and methods which may selectively restrict air from entering certain portions of the lungs or other organs. For example, when placed in a portion of one or more lungs, the devices disclosed herein may allow air to enter a section of the lungs at one time and restrict air from entering at another time. In another example, multiple valve devices may be implanted at different sections of the lungs to allow air to enter a first section of the lungs while restricting air from entering other parts of the lungs, thereby allowing the first section of the lungs more space to expand during inhalation.

The device and system may also be used to selectively control which parts of the lungs, or any other organ into which the device is placed, are exposed to smoke. e.g. during inhalation of cigarette smoke, and further may be used to control and maintain air velocity for COPD patients. In addition, the device, system and method may be used to reduce or prevent inhalation of other contaminants from entering portions of the lung or any other organs into which the device is placed. For example, the device may be used to prevent or reduce inhalation of noxious and/or toxic fumes, and/or gases by those working in an environment in which potentially harmful or irritating gases or fumes are present. For instance, the device may be used by workers in oil fields and mines, workers handling waste products, fire-fighters to prevent exposure to smoke, toxic fumes, odors, and other contaminants, and anyone exposed to harmful contaminants.

The device may also be used to choke air flow above a certain flow-rate, such that a flow-condition is created similar to that achieved by applying the "Rescue Technique" in which a gentle force is applied to a patient's chest to force expiration or air. This technique helps correct dynamic hyperinflation by gently forcing air out of the lungs, thereby reducing both the internal chest pressure as well as the air velocity through the bronchial tubes. The device may be placed downstream in larger bronchial tubes such that air velocity remains under a certain threshold, this is in contrast to COPD patients in whom the bronchial tube may collapse above a certain flow rate. The device may limit air velocity to remain under a value lower than the critical flow at which most bronchioles may collapse. The device may include a membrane which moves inwards when air flow in increased. This configuration may allow flow resistance to increase gradually with increasing air flow so that air flow may remain (choked) under a certain maximum. The membrane may be configured to not fully close so as to maintain an air-duct through the device, allowing a low flow-rate to be maintained, similar to the flow rate achieved by the Rescue Technique.

In the above overview, the lung is only used as an example and the disclosed devices may be used in other organs of the body. Various embodiments herein may include one or more features of other disclosed embodiments.

Exemplary Embodiments

FIGS. 1A and 1B illustrate two side views of an exemplary valve device 100 for controlling air flow according to embodiments of the present disclosure. Particularly, FIG. 1A illustrates valve device 100 in a relaxed position and FIG. 1B illustrates the valve device 100 in a contracted position.

Valve device 100 may include a substantially circular cross-section or it may have a cross-section similar to that of body cavities such that it may occupy a desired space in the body. Accordingly, where required by given applications, valve device 100 may include elliptical, semi-circular, rhombic, rectangular, or any other suitable profile. Moreover, the diameter of valve device 100 may vary based on the size of the body lumens in which it operates. In addition, the cross-sectional geometry of valve device 100 may vary along its length. The valve device 100 may include a lumen 105 between the valve device 100 distal 170 and proximal 180 ends.

The lumen 105 may have any suitable size and shape, including circular, elliptical, semi-circular, rhombic, or rectangular. The size and shape of the lumen 105 may be constant or may vary along its length.

The valve device 100 may include a wire frame 110 made of any suitable material for implantation in the body. Such materials may include metals, including, for example, stainless steel or other alloys and/or may include any suitable shape-memory material, including metal and/or polymeric materials, such as nitinol or polyurethane based memory polymers. The wire frame 110 may be capable of self-expanding. For example, the wire frame 110 may include a plurality of wires having one or more shape memory materials interconnected to form a stent-like configuration. This may allow the wire frame 110 to be in a collapsed position during placement of the valve device 100, and then subject to self-expansion upon placement due to the shape memory properties of the shape memory materials.

In another embodiment, the wire frame 110 may be non-self-expanding. For example, the wire frame may include a plurality of wires interconnected to form a stent-like configuration in a compressed or crimped configuration and may be expanded by any suitable mechanism upon delivery of the device or any time thereafter. For example, the compressed non-self-expanding wire frame 110 may be delivered to the desired location in the compressed configuration using a delivery device. An expandable member, such as a delivery device having an expandable portion may be inserted into the wire frame 110 lumen 105 and expanded, thereby expanding the wire frame 110 and then removed from the wire frame 110. For example, the delivery device may be a catheter having an expandable portion, such as an expandable balloon and the wire frame 110 may be placed over the unexpanded device. The expandable device, such as a balloon catheter may be expanded, thereby expanding the wire frame 110 to the desired diameter. The balloon catheter may then be deflated and removed from the expanded wire frame 110.

The wire frame 110 may include barbs, tines and/or other protrusions to allow implantation, removal and/or anchoring of the valve device 100 in the desired location. For example, the wire frame 110 may include a tine or other suitable protrusion (e.g. a hook or loop) that may engage with implantation and/or removal tools so as to allow the wire frame 110 to be expanded or collapsed, for example using a pull wire. In addition, an outer surface of valve device 100 may include one or more barbs for engaging adjacent tissue to facilitate retaining the valve device 100 in a desired location.

The wire frame 110 may include an outer cover 120 having a sufficient rigidity to maintain a tubular configuration on the wire frame 110. The outer cover 120 may extend along the entire length or only along one or more portions of the wire frame 110. The outer cover 120 may extend completely around or only partially around the wire frame 110. The material used to manufacture the outer cover 120 may include a flexible material and exemplary embodiments may include polytetrafluoroethylene (PTFE), polyethylene, FEP (fluorinated ethylene propylene), ETFE (ethylene tetrofluoroethylene), polypropylene, polysulfone, polyethylene, polyethersulfone, silicone, silicon rubber, etc. The outer cover 120 may include a coating having, for example, lubricious, and/or therapeutic properties (e.g. antibiotic, anti-inflammatory, anesthetic), and may be porous. In addition, the outer cover 120 may be radiopaque and/or may include markings to allow visualization under x-ray or fluoroscopy.

Valve device 100 may include an inner membrane 130 along at least a portion of the inside of the wire frame 110. The inner membrane 130 may have elastic properties. The material used to manufacture the inner membrane 130 may include a flexible material and exemplary embodiments may include polytetrafluoroethylene (PTFE), polyethylene, FEP (fluorinated ethylene propylene), ETFE (ethylene tetrofluoroethylene), polypropylene, polysulfone, polyethylene, polyethersulfone, silicone, silicon rubber, etc. The inner membrane 130 may have a uniform flexibility or have varying flexibilities along the inner membrane 130. For example, the inner membrane 130 may be more flexible at a central portion. The inner membrane 130 may have the same or different flexibility as the outer cover 120.

The inner membrane 130 may be provided at one or more continuous or non-continuous portions of the valve device 100, for example, at a distal end 170, and/or proximal end 180, or any other portions or combination of portions inside the valve device 100. For example, as shown in FIGS. 1A and 1B, inner membrane 130 may be provided inside a proximal portion 180 of the valve device 100. The inner membrane 130 and may have a round, triangular shape or any other suitable shape, geometry, size or orientation.

The valve device 100 may include one or more actuation components 140 that may change from a first non-actuated state to a second actuated state. The actuation components 140 may be directly or indirectly connected to a portion of the inner membrane 130 by any suitable means, such that when actuated, the actuation components 140 may cause a change in the amount of inner lumen 105 space the inner membrane 130 occupies, thereby transitioning the inner lumen 105 from a first diameter to a second smaller diameter, thereby narrowing at least a portion of the lumen 105. For example, when actuated, the actuation component 140 may cause the inner membrane 130 to expand and thereby increasing the amount of inner lumen 105 space the inner membrane 130 occupies.

The actuation components 140 may take any suitable composition, size shape, geometry or orientation. Adjacent actuation components 140 may be uniformly or non-uniformly spaced apart on the valve device 100. Any suitable means may be used to dispose the actuation components 140 on the valve device 100, including, but not limited to: printing, adhesive, or embossing.

In the exemplary embodiment shown in FIGS. 1A and 1B, portions of the inner membrane 130 may include or be connected to actuation components 140 that may change from a first non-actuated state (FIG. 1A) to a second actuated state (FIG. 1B), such that the actuated state causes at least a portion of the inner membrane 130 having a flap-like form, to bias from a first configuration to a second configuration. For example, the actuated state may cause the inner membrane 130 to expand and occupy a greater portion of the lumen 105 (FIG. 1B) than when in the non-actuated state, and narrow at least a portion of the lumen 105.

The actuation components 140 may be configured to limit the amount of space of the inner lumen 105 that the inner membrane 130 occupies when it is expanded by the actuated actuation components 140 so as to prevent the lumen 105 from being fully blocked by the inner member 130.

Examples of actuation mechanisms that may actuate the actuation components 140 may include, but are not limited to: electro-active polymer (EAP) actuation, pneumatic actuation (e.g., compressed air/gas), electrical actuation, hydraulic actuation, piezoelectric actuation, thermal actuation, electrostatic actuation, magnetic actuation, inductive actuation, actuation by the body's own forces (e.g. during breathing), and any other suitable actuation methods.

The embodiments shown in FIGS. 2A and 2B may include any of the components or features of the embodiments described in reference to FIGS. 1A and 1B.

Valve device 200 may include a substantially circular cross-section or it may have a cross-section similar to that of body cavities such that it may occupy a desired space in the body. Accordingly, where required by given applications, valve device 200 may include elliptical, semi-circular, rhombic, rectangular, or any other suitable profile. Moreover, the diameter of valve device 200 may vary based on the size of the body lumens in which it operates. In addition, the cross-sectional geometry of valve device 200 may vary along its length.

The valve device 200 may include a wire frame 210 made of any suitable material such as a metal, for example, stainless steel or other alloy and/or may include any suitable shape-memory material including metal and/or polymeric material, such as nitinol or polyurethane based memory polymers. The wire frame 210 may be capable of self-expanding. For example, the wire frame 210 may include a plurality of wires interconnected to form a stent-like configuration with a lumen 205. This may allow the wire frame 210 to be in a collapsed position during placement of the valve device, and then subject to self-expansion upon placement.

In another embodiment, the wire frame 210 may be non-self-expanding. For example, the wire frame may include a plurality of wires interconnected to form a stent-like configuration in a compressed or crimped configuration and may be expanded by any suitable mechanism upon delivery of the device or any time thereafter. For example, the compressed non-self-expanding wire frame 210 may be delivered to the desired location in the compressed configuration using a delivery device. A device having an expandable portion, such as the delivery device or any other device having an expandable portion may be inserted into the wire frame 210 and expanded, thereby expanding the wire frame 210 and then removed from the wire frame 210. For example, the delivery device may be a catheter having an expandable portion, such as an expandable balloon and the wire frame 210 may be placed over the unexpanded balloon catheter. The expandable device, such as a balloon catheter may be expanded, thereby expanding the wire frame 210 to the desired diameter. The balloon catheter may then be deflated and removed from the wire frame 210.

The wire frame 210 may include barbs, tines and/or other protrusions to allow implantation, removal and/or anchoring of the valve device 200 in the desired location. For example, the wire frame 210 may include a tine or other suitable protrusion (e.g. a hook or loop) that may engage with implantation and/or removal tools so as to allow the wire frame 210 to be expanded or collapsed, for example using a pull wire. In addition, an outer surface of valve device 200 may include one or more barbs for engaging adjacent tissue to facilitate retaining the valve device 200 in a desired location.

The wire frame 210 may include an outer cover 220 having a sufficient rigidity to maintain a tubular configuration on the wire frame 210. The outer cover 220 may extend along the entire length or only along one or more portions of the wire frame 210. The outer cover 220 may extend completely around or only partially around the wire frame 210. The material used to manufacture the outer cover 220 may include a flexible material and exemplary embodiments may include polytetrafluoroethylene (PTFE), polyethylene, FEP (fluorinated ethylene propylene), ETFE (ethylene tetrofluoroethylene), polypropylene, polysulfone, polyethylene, polyethersulfone, silicone, silicon rubber, etc. The outer cover 220 may include a coating having, for example, lubricious, and/or therapeutic properties (e.g. antibiotic, anti-inflammatory, anesthetic), and may be porous. In addition, the outer cover 220 may be radiopaque and/or may include markings to allow visualization under x-ray or fluoroscopy.

Valve device 200 may include an inner membrane 230 along at least a portion of the inside of the wire frame 210. The inner membrane 230 may have elastic properties. The material used to manufacture the inner membrane 230 may include a flexible material and exemplary embodiments may include polytetrafluoroethylene (PTFE), polyethylene, FEP (fluorinated ethylene propylene), ETFE (ethylene tetrofluoroethylene), polypropylene, polysulfone, polyethylene, polyethersulfone, silicone, silicon rubber, etc. The inner membrane 230 may have a uniform flexibility or have varying flexibilities. For example, the inner membrane 230 may be more flexible at a central portion. The inner membrane 230 may have the same or different flexibility as the outer cover 220.

The inner membrane 230 may be provided at one or more continuous or non-continuous portions of the valve device 200. For example, as shown in FIGS. 2A and 2B, inner membrane 230 may be provided along the length of the valve device 200. The inner membrane 230 and may have a round, triangular shape or any other suitable shape, geometry, size or orientation.

The valve device 200 may include one or more stretchable components 240 that may change from a first non-elongated state to a second elongated state. The stretchable components 240 may be directly or indirectly connected to a portion of the inner membrane 230 by any suitable means, such that when elongated, they may cause a change in the amount of inner lumen 205 space the inner membrane 230 occupies, thereby narrowing at least a portion of the lumen 205. For example, when elongated, the stretchable components 240 may cause the inner membrane 230 to expand, thereby increasing the amount of inner lumen 205 space the inner membrane 230 occupies. In turn, the inner lumen 205 transitions from a first diameter to a second diameter that is smaller than the first diameter.

The stretchable components 240 may take any suitable composition shape, geometry or orientation. Adjacent components 240 may be uniformly or non-uniformly spaced apart on the valve device 200. Any suitable means may be used to dispose the components 240 on the valve device 100, including, but not limited to: printing, using adhesive, or embossing.

As shown in FIGS. 2A and 2B, an example of stretchable components 240 that may change from a non-elongated state (FIG. 2A) to second elongated state (FIG. 2B) such that the elongated state causes at least a portion of the inner membrane 230, which may be formed along the valve device 200, to occupy the lumen 205 and narrow at least a portion of the lumen 205, may be an elastic fiber network 240 having various expansion amounts.

The stretchable components 240 may be manufactured from any suitable material that may stretch from a non-elongated state to an elongated state and may function in accordance with Bernoulli's Principle. Bernoulli's Principle states that as the speed of a moving fluid increases, the pressure within the fluid decreases. As such, the lumen 205 of the valve device 200 may have a certain pressure and if this pressure drops, the inner membrane 230 may collapse inwards, thereby closing the lumen 205. The stretchable components 240 may prevent the lumen 205 from being fully closed by the inner membrane 230 by being configured to reach their elastic limit, e.g. the maximum amount the stretchable components 240 may elongate, before the lumen 205 is fully closed by the inner membrane 230. For example, the stretchable components 240 may act as strain limiting factors. For instance, the stretchable components 240 may be manufactured by extrusion or a casting a tube made of a flexible soft polymer, for example a very low durometer polyurethane. Holes may then be made in the wall of the tube, using, for example, an excimer laser, such that only thin walls between the holes remain. A polymer sheath may then be adhered to the inside this open structure. In a similar manner, a polymer sheath may be adhered around the outside of the tube. In addition, the outer and inner sheath may be adhered together at both ends to make a closed construction. In addition, or alternatively, the stretch component 240 may be formed by any other suitable method. For example, a thin flexible polymer material may be formed into a tube and folded in half, similar to a sock, and placed inside a hole. A pin may then be inserted through the middle of the folded flexible polymer material and a polymer foam may be injected in the formed double layer that adheres to both surfaces, forming a stretch component 240 network between two sides of an inner membrane 230.

Figure 3A:
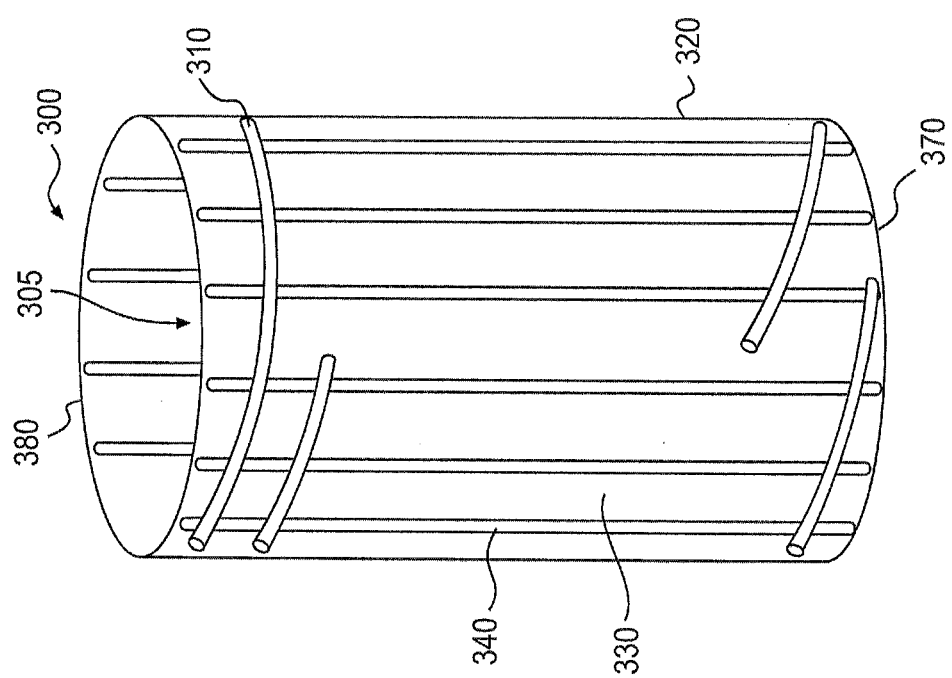

The embodiments shown in FIGS. 3A and 3B may include any of the components or features of the embodiments described in reference to FIGS. 1A,1B, 2A and, 2B.

Valve device 300 may include a substantially circular cross-section or it may have a cross-section similar to that of body cavities such that it may occupy a desired space in the body. Accordingly, where required by given applications, valve device 300 may include elliptical, semi-circular, rhombic, rectangular, or any other suitable profile. Moreover, the diameter of valve device 300 may vary based on the size of the body lumens in which it operates. In addition, the cross-sectional geometry of valve device 300 may vary along its length.

The valve device 300 may include a wire frame 310 made of any suitable material such as a metal, for example, stainless steel or other alloy and/or may include any suitable shape-memory material, including metal and/or polymeric materials, such as nitinol or polyurethane based memory materials. The wire frame 310 may be capable of self-expanding. For example, the wire frame 310 may include a plurality of wires interconnected to form a stent-like configuration with a lumen 305. This allows the wire frame 310 to be in a collapsed position during placement of the valve device, and then subject to self-expansion upon placement.

In another embodiment, the wire frame 310 may be non-self-expanding. For example, the wire frame may include a plurality of wires interconnected to form a stent-like configuration in a compressed or crimped configuration and may be expanded by any suitable mechanism upon delivery of the device or any time thereafter. For example, the compressed non-self-expanding wire frame 310 may be delivered to the desired location in a compressed configuration using a delivery device. A device having an expandable portion, such as the delivery device may be inserted into the wire frame 310 and expanded, thereby expanding the wire frame 310 and then removed from the wire frame 310. For example, the delivery device may be a catheter having an expandable portion, such as an expandable balloon and the wire frame 310 may be placed over the unexpanded balloon catheter. The expandable portion, such as a balloon catheter may be expanded, thereby expanding the wire frame 310 to the desired diameter. The balloon catheter may then be deflated and removed from the wire frame 310.

The wire frame 310 may include barbs, tines and/or other protrusions to allow implantation, removal and/or anchoring of the valve device 300 in the desired location. For example, the wire frame 310 may include a tine or other suitable protrusion (e.g. a hook or loop) that may engage with implantation and/or removal tools so as to allow the wire frame 310 to be expanded or collapsed, for example using a pull wire. In addition, an outer surface of valve device 300 may include one or more barbs for engaging adjacent tissue to facilitate retaining the valve device 300 in a desired location.

The wire frame 310 may include an outer cover 320 having a sufficient rigidity to maintain a tubular configuration on the wire frame 310. The outer cover 320 may extend along the entire length or only along one or more portions of the wire frame 310. The outer cover 320 may extend completely around or only partially around the wire frame 310. The material used to manufacture the outer cover 320 may include a flexible material and exemplary embodiments may include a flexible material and exemplary embodiments may include polytetrafluoroethylene (PTFE), polyethylene, FEP (fluorinated ethylene propylene), ETFE (ethylene tetrofluoroethylene), polypropylene, polysulfone, polyethylene, polyethersulfone, silicone, silicon rubber, etc. The outer cover 320 may include a coating having, for example, lubricious, and/or therapeutic properties (e.g. antibiotic, anti-inflammatory, anesthetic), and may be porous. In addition, the outer cover 320 may be radiopaque and/or may include markings to allow visualization under x-ray or fluoroscopy.

Valve device 300 may include an inner membrane 330 along at least a portion of the inside of the wire frame 310. The inner membrane 330 may have elastic properties. The material used to manufacture the inner membrane 330 may include a flexible material and exemplary embodiments may include a flexible material and exemplary embodiments may include polytetrafluoroethylene (PTFE), polyethylene, FEP (fluorinated ethylene propylene), ETFE (ethylene tetrofluoroethylene), polypropylene, polysulfone, polyethylene, polyethersulfone, silicone, silicon rubber, etc. The inner membrane 330 may have a uniform flexibility or have varying flexibilities. For example, the inner membrane 330 may be more flexible at a central portion. The inner membrane 330 may have the same or different flexibility as the outer cover 320.

The valve device 300 may include one or more actuation components 340 that may change from a first non-actuated state to a second actuated state. The actuation components 340 may be directly or indirectly connected to a portion of the inner membrane 330 by any suitable means, such that when actuated, the actuation components 340 may cause a change in the amount of inner lumen 305 space the inner membrane 330 occupies, thereby narrowing at least a portion of the lumen 305. For example, when actuated, the actuation component 340 may cause the inner membrane 330 to expand and thereby increasing the amount of inner lumen 305 space the inner membrane 330 occupies. In turn, the inner lumen 305 transitions from a first diameter to a second diameter that is smaller than the first diameter.

The actuation components 340 may take any suitable composition shape, geometry or orientation. Adjacent actuation components 340 may be uniformly or non-uniformly spaced apart on the valve device 300. Any suitable means may be used to dispose the actuation components 340 on the valve device 300, including, but not limited to: printing, using adhesive, or embossing.

As described above, the actuation of the actuation components 340 may be accomplished by any suitable mechanism. Examples of such actuation mechanisms may include, but are not limited to: electro-active polymer (EAP) actuation, pneumatic actuation (e.g., compressed air/gas), electrical actuation, hydraulic actuation, piezoelectric actuation, thermal actuation, electrostatic actuation, magnetic actuation, inductive actuation, the body's own forces, and any other suitable actuation methods.

Adjacent actuation components 340 may be uniformly or non-uniformly spaced apart on the valve device and may comprise a material that exhibits a change in state, size, shape, geometry, orientation or any other change when subjected to a stimulus.

For example, the actuation components 340 may include an EAP component. The actuation components 340 may have any suitable shape, size (length, thickness, width) orientation or geometry. For example, as shown in FIGS. 3A and 3B, the actuation components 340 may include EAP material(s) having a stripe like shape or other suitable shape, configuration, or geometry. The actuation components 340 may be oriented in a vertical, horizontal, oblique angle, acute angle, or any other orientation and may be spaced at regular or irregular intervals along the inner membrane 330. The number and amount of space between each of the actuation components 340 may be varied depending on the amount of bending and the shape required of the contracted inner membrane 330. The actuation components 340 may be disposed the around the entire length of the valve device 300 or along portions of the valve device 300. The actuation components 340 may be disposed all the way around the valve device 300 or partially around the valve device 300.

The actuation components 340 may be disposed by any suitable means on the valve device 300, for example, via printing, using adhesive, or embossing. FIGS. 3A and 3B show an example of using an actuation configuration in which the actuation components 340 may be disposed on the inner membrane 330 of the valve device 300. In an exemplary embodiment, actuation components 340 may be printed on the inner membrane 330 using a inkjet or any other suitable type of printing. The actuation components 340 may include an EAP and the EAP may cycle at frequencies up to about 5 Hz, which may be well beyond normal breathing frequencies.

When subjected to a power source, such as for example, an electric field, the actuation components 340 may change (e.g. bend, contract, stretch, expand, swell, harden, soften) due to ionic absorption or molecular attraction.

The actuation components 340 may include electronic, ionic and/or elecstrictive, or any other suitable type of EAR Some commonly known EAPs include, but are not limited to, polypyrroles, polyanilines, polythiophenes, polyethylenedioxythiophenes, poly(p-phenylene vinylene)s, polysulfones and polyacetylenes.

For example, the actuation components 340 may include an ionic liquid EAP, for example polypyrole, which may have similar strength properties to human muscle, and/or other conjugated polymers, such as, polyaniline, poly(ethylenedioxythiopene). The actuation components 340 may swell and may switch between an actuated and non-actuated state within a desired time period, for example, within 1-10 or 1-5 seconds. The power consumption of the EAP may be low, such as less than 1 volt.

One or more portions of each of the actuation components 340 may be connected to an electrode 350 which in turn may be connected to a power source. For example, portions adjacent both ends of each actuation component 340 may be connected to an electrode 350. Examples of the power source may include an internal or external battery, or internal or external capacitor. The power source 360 may activate the actuation components 340, allowing them to change states.

For example, as explained in Mirfakhrai et al., *Polymer artificial muscles*. Mater. Today (Netherlands), vol. 10, no. 4, pp. 30-38, 2007, the contents of which are incorporated by reference herein, according to a dielectric EAP (DEAP) principle, a voltage may be applied to electrodes 350 connected to different portions of an elastomer. The electrostatic forces generated by the voltage may squeeze the elastomer. Since elastomers have a Poisson coefficient close to about 0.5, the whole structure may stretch.

Each of the actuation components 340 may be actuated to change states at any point or portion of the actuation component 340. For example, as shown in FIG. 3B, actuation members 340 may be actuated and may bend at one or more points approximately half-way between the distal end 370 and proximal end 380 of the valve device 300.

The shape, geometry and orientation of the inner membrane 330 formed by the actuated members 340 may vary depending on the amount and location of the actuation or contracting of the actuated members 340. For example, as shown in FIG. 3B, the inner membrane 330 may form an hour-glass like shape when the actuation components 340 are actuated.

Each of the actuation components 340 may comprise the same or different type of composition. The amount that the actuation components 340 may deflect/bend may be controlled by the amount of power supplied, the composition of the actuation components and/or the size (length, width, thickness).

In another example, the inner membrane 330 may be switched between relaxed and contracted positions by using the body's own forces e.g. by inhalation/expiration airstreams. Alternatively, an external power source may be used to actuate the valve 300. For example through an inductive system, an optical energy system or any other suitable system. A coupling element, such as a receiver or photovoltaic cell, or any other suitable coupling element may be placed in an upper part of the trachea, by for example, placing an implantable structure, such as a stent or any other suitable implantable structure. The coupling element may have an electrically conductive wire or other conductive element connected to the valve device. The coupling element may receive power from an external power source, such as a battery or capacitor.

A rechargeable element may be in close proximity to the coupling element. For example, the rechargeable element may be worn on or close to the neck, such as in the form of a necklace, neck brace, or other form, so as to couple energy to the receiver. Alternatively, or additionally, the receiver may be placed around the patient's chest via a belt, or a pillow place under the patient's head, or other suitable form.

The contracted state of the inner membrane 330, when the actuation components 340 are actuated, may allow air to leave the valve device 300 from the distal end 370, but prevent air from entering from the proximal end 380. In this manner, inhaled air or other inhaled contaminants may be prevented from entering a portion of the lungs where the valve device 300 is placed.

Figure 4A:
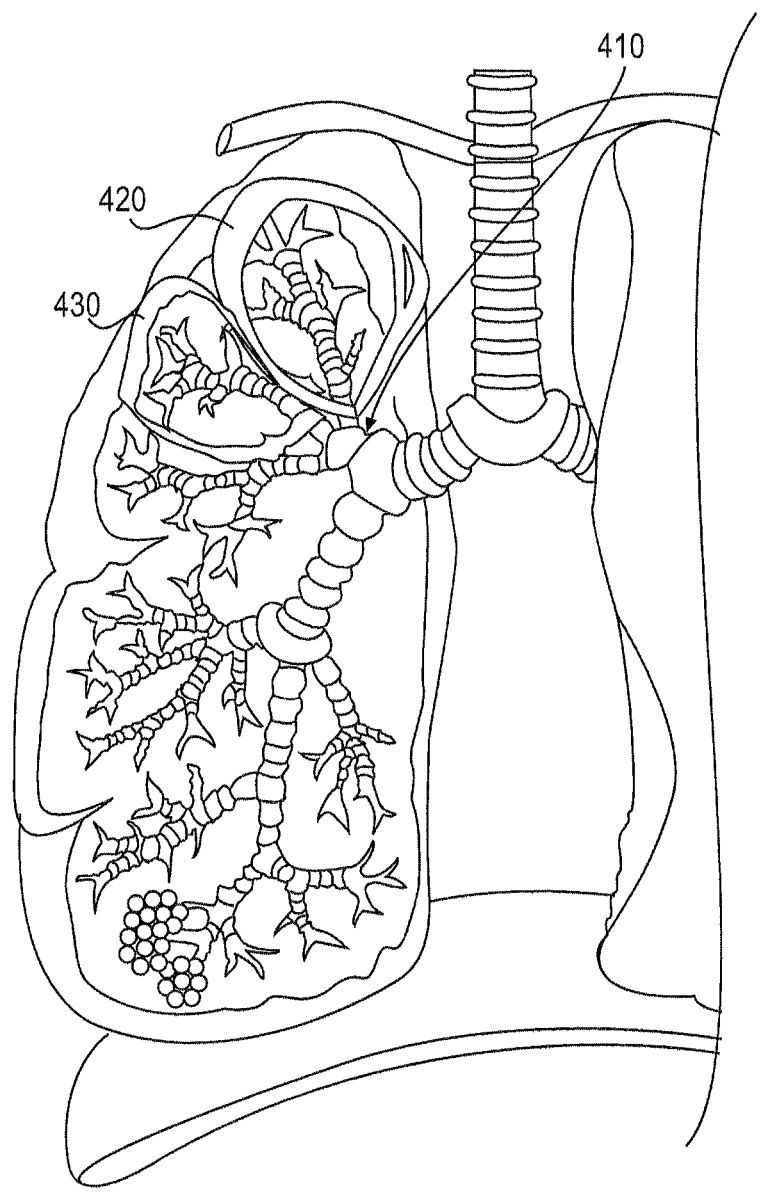
FIG. 4A illustrates exemplary regions of a lung into which exemplary embodiments of valve devices disclosed herein may be placed, according to an embodiment of the present disclosure.

As shown in FIG. 4A, the valve devices described herein may be placed via any suitable minimally invasive method at e.g., a bronchial inlet 410 to a lobe 420 of a lung. In an exemplary embodiment, the valve devices may be in a collapsed state and may be placed with a delivery mechanism, which may in turn be placed into a steerable bronchoscope. The delivery mechanism may include a hollow tube such as a catheter having a guide wire or any other suitable delivery means.

Figure 4B:
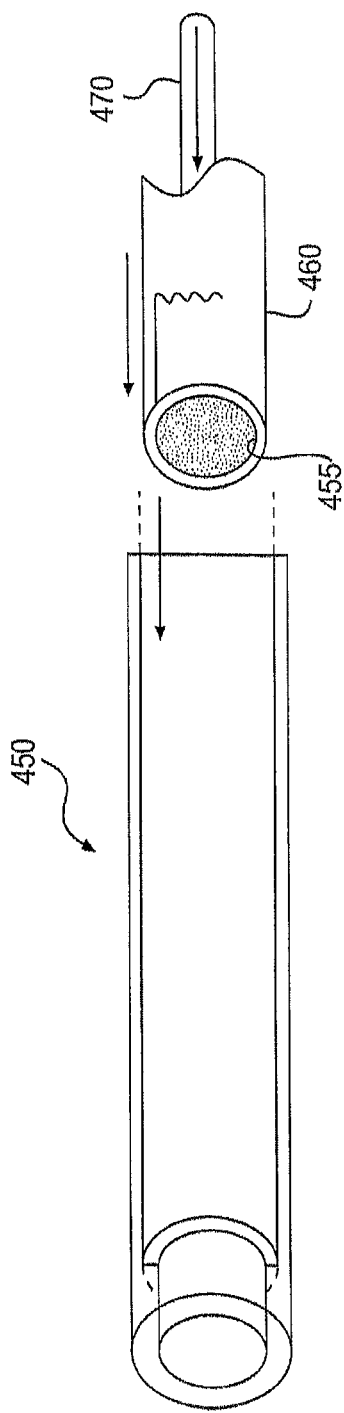
FIGS. 4B and 4C are views of a delivery device, according to another embodiment of the present disclosure.
Figure 4C:
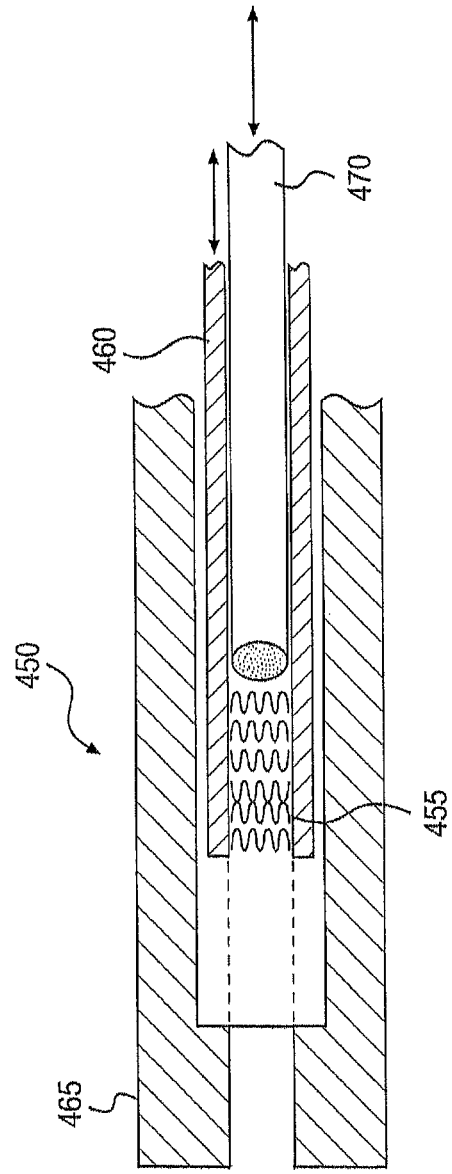

The bronchoscope may be inserted into the airways, such as through the nose or mouth, or through a tracheostomy. The valve devices may be then pushed out of the carrier and into position via any suitable means. For example, as shown in FIGS. 4B and 4C, multiple valve devices may be deployed using a single delivery device, such as a bronchoscope 450. The valve devices 455 may be in a compressed form and may be inserted at a proximal end of the bronchoscope 450 and pushed along the length of the bronchoscope 450 towards the distal end of the bronchoscope 450, from which end the valve devices 455 may deploy. Each valve devices 455 may be premounted (e.g. compressed) in a polymer housing tube 460 made of any suitable material, such as PET or PTFE, so that the housing tubes 460 may slide through the lumen of the bronchoscope 450 with reduced friction.

The bronchoscope 450 may include a distal ring 465 in the lumen of the bronchoscope 450 having the same inner diameter as the inner diameter of the housing tubes 460 of the valve device 455. The distal ring 465 may be configured to restrict or block the housing tubes 460 from being pushed out of the bronchoscope 450. Once the housing tubes 460 are at the distal end of the bronchoscope 450, the housing tubes 460 may be pushed through the lumen of the bronchoscope 450 with a push rod 470. The push rod 470 may have the same diameter as the inner diameter of the housing tubes 460.

Alternatively, multiple valve devices 455, may be prepackaged in a single individual housing tube 460 and once the bronchoscope is located, the single housing tube may be pushed through the lumen of the bronchoscope 450 until the housing tube 460 reaches the distal inner ring 465. The pushrod 470 may then be used to push a valve device 455 out of the distal end of the bronchoscope 450, so that it may self-expand and this procedure may be repeated multiple times for each valve device 455 loaded in the housing tube.

The valve devices may contract as described above, preventing inhaled air from entering the lobe 420. Multiple valve devices may be placed near a common bronchial inlet 410 at the inlets of adjacent lobes 420, 430 as desired. The multiple valve devices serving the adjacent lobes 420 and 430 may be selectively relaxed and closed in controlled manner, e.g. if the valve device serving lobe 420 is relaxed, the valve device serving lobe 430 may be closed. When the valve devices 400 are not supplied with a power source (e.g. electrical, pneumatic, magnetic, fluidic, the body's own forces), the relaxed or normal state, the valve devices may allow both inhalation and exhalation.

Figure 5A:
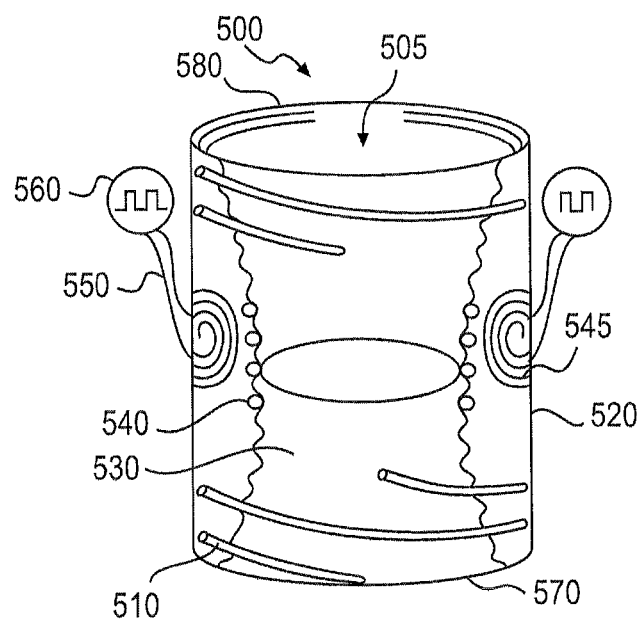
FIGS. 5A and 5B are views of a valve device, according to another embodiment of the present disclosure.
Figure 5B:
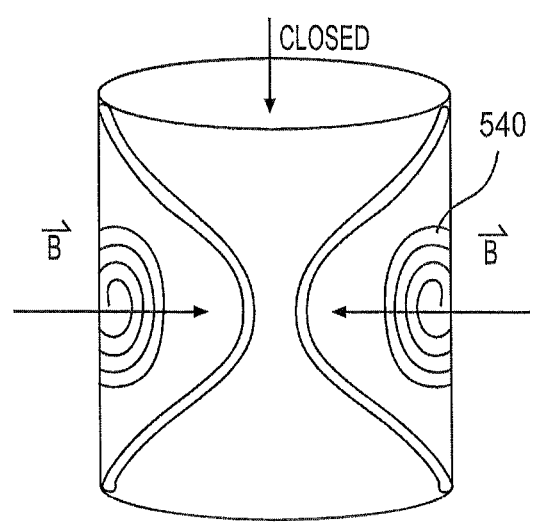

The embodiments shown in FIGS. 5A and 5B may include any of the components or features of the embodiments described in reference to FIGS. 1A-3B.

Valve device 500 may include a substantially circular cross-section or it may have a cross-section similar to that of body cavities such that it may occupy a desired space in the body. Accordingly, where required by given applications, valve device 500 may include elliptical, semi-circular, rhombic, rectangular, or any other suitable profile. Moreover, the diameter of valve device 500 may vary based on the size of the body lumens in which it operates. In addition, the cross-sectional geometry of valve device 500 may vary along its length.

The valve device 500 may include a wire frame 510 made of any suitable material such as a metal, for example, stainless steel or other alloy and/or may include any suitable shape-memory material, including metal and/or polymeric materials, such as nitinol or polyurethane based memory polymers. The wire frame 510 may be capable of self-expanding. For example, the wire frame 510 may include a plurality of wires interconnected to form a stent-like configuration with a lumen 505. This allows the wire frame 510 to be in a collapsed position during placement of the valve device, and then subject to self-expansion upon placement.

In another embodiment, the wire frame 510 may be non-self-expanding. For example, the wire frame may include a plurality of wires interconnected to form a stent-like configuration in a compressed or crimped configuration and may be expanded by any suitable mechanism upon delivery of the valve device or any time thereafter. For example, the compressed non-self-expanding wire frame 510 may be delivered to the desired location in the compressed configuration using a delivery device. A device having an expandable portion, such as the delivery device, may be inserted into the wire frame 510 lumen 505 and the expandable portion may be expanded, thereby expanding the wire frame 510. The device may then be removed from the expanded wire frame 510. For example, the delivery device may be a catheter having an expandable portion, such as an expandable balloon and the wire frame 510 may be placed over the unexpanded balloon catheter. The expandable device, such as a balloon catheter may be expanded, thereby expanding the wire frame 510 to the desired diameter. The balloon catheter may then be deflated and removed from the wire frame 510.

The wire frame 510 may include barbs, tines and/or other protrusions to allow implantation, removal and/or anchoring of the valve device 500 in the desired location. For example, the wire frame 510 may include a tine or other suitable protrusion (e.g. a hook or loop) that may engage with implantation and/or removal tools so as to allow the wire frame 510 to be expanded or collapsed, for example using a pull wire. In addition, an outer surface of valve device 500 may include one or more barbs for engaging adjacent tissue to facilitate retaining the valve device 500 in a desired location.

The wire frame 510 may include an outer cover 20 having a sufficient rigidity to maintain a tubular configuration on the wire frame 510. The outer cover 520 may extend along the entire length or only along one or more portions of the wire frame 510. The outer cover 520 may extend completely around or only partially around the wire frame 510. The material used to manufacture the outer cover 520 may include a flexible material and exemplary embodiments may include a flexible material and exemplary embodiments may include polytetrafluoroethylene (PTFE), polyethylene, FEP (fluorinated ethylene propylene), ETFE (ethylene tetrofluoroethylene), polypropylene, polysulfone, polyethylene, polyethersulfone, silicone, silicon rubber, etc.

The outer cover 520 may include a coating having, for example, lubricious, and/or therapeutic properties (e.g. antibiotic, anti-inflammatory, anesthetic), and may be porous. In addition, the outer cover 520 may be radiopaque and/or may include markings to allow visualization under x-ray or fluoroscopy.

Valve device 500 may include an inner membrane 530 along at least a portion of the inside of the wire frame 510. The inner membrane 530 may have elastic properties. The material used to manufacture the inner membrane 530 may include a flexible material and exemplary embodiments may include a flexible material and exemplary embodiments may include polytetrafluoroethylene (PTFE), polyethylene, FEP (fluorinated ethylene propylene), ETFE (ethylene tetrofluoroethylene), polypropylene, polysulfone, polyethylene, polyethersulfone, silicone, silicon rubber, etc. The inner membrane 530 may have a uniform flexibility or have varying flexibilities. For example, the inner membrane 530 may be more flexible at a central portion. The inner membrane 530 may have the same or different flexibility as the outer cover 520.

The valve device 500 may include one or more actuation components 540 that may change from a first non-actuated state to a second actuated state. The actuation components 540 may be directly or indirectly connected to a portion of the inner membrane 530 by any suitable means, such that when actuated, the actuation components 540 may cause a change in the amount of inner lumen 505 space the inner membrane 530 occupies, thereby narrowing at least a portion of the lumen 505. For example, when actuated, the actuation component 540 may cause the inner membrane 530 to expand and thereby increasing the amount of inner lumen 505 space the inner membrane 130 occupies. In turn, the inner lumen 505 may transition from a first diameter to a second diameter that is smaller than the first diameter.

As shown on FIGS. 5A and 5B, an example of an actuation component 540 that may change from a non-actuated stated (FIG. 5A) to a second actuated state (FIG. 5B) such that the actuated state causes at least a portion of the inner membrane 530 to increase the amount of lumen 505 space it occupies and reduce the diameter of at least a portion of the lumen 505, may be a material that exhibits a change in size or shape when subject to a stimulus.

The actuation components 540 may take any suitable composition shape, geometry and/or orientation. Adjacent actuation components 540 may be uniformly or non-uniformly spaced apart on the valve device 500. Any suitable means may be used to dispose the actuation components 540 on the valve device 500, including, but not limited to: printing, using adhesive, or embossing.

The actuation components 540 may be disposed on one or more portions along the length of the valve device 500 to contract the inner membrane 530 and thereby restrict or block air or any other contaminant from entering through the valve device 500. The one or more actuation components 540 may disposed on different positions along the length of the valve device 500 and may be equal or unequal in number and size on each side of the valve device 500. For example, as shown in FIG. 5A, actuation components 540 disposed on opposite sides of the valve device 500 may be equal in number and size. The actuation components 540 may cause the inner membrane 530 to contract and transition the lumen 505 from a first diameter to a second diameter smaller than the first, when actuated.

In the embodiment shown in FIG. 5A, the actuation components 540 may include one or more components having magnetic properties having any suitable shape geometry, and orientation. For example, the actuation components 540 having magnetic properties may be permanent magnetic dots markers. These actuation components 540 may be activated using a current source. For example, one or more current conducting element 545 having any suitable shape, geometry, and orientation may be placed on or adjacent to the outer cover 520 of the valve device 500 device at a proximity close to the actuation component 540. In the example shown in FIGS. 5A and 5B, the current conducting element(s) 545 may be a wire coil. The wire coil may be manufactured with any suitable material such as stainless steel, copper, nitinol, or any other suitable material.

The current conducting element(s) 545 may be connected to an electrode 550, which in turn may be connected to a current producing power source 560. The current conducting element(s) 545 may be activated by the power source 560 and cause a repulsive magnetic force between the current conducting element(s) 545 and the actuation component(s) 540, thereby causing the inner membrane 530 to contract. The current conducting element(s) 545 may attract and repel the actuation component(s) 540 depending on the polarity of the current conducting element(s) 545. A reverse current from the power source 560 may cause an attractive magnetic force between the current conducting element(s) 545 and the actuation component(s) 540, thereby causing the inner membrane 530 to return to a relaxed configuration.

In another embodiment, a current conducting element 545 having any suitable shape, geometry, and/or orientation may be disposed on or adjacent to the outer cover 520 of the valve device 500 device at a proximity close another current conducting element 545 that may be disposed on the inner membrane 530. The current conducting element 545 disposed on or adjacent to the outer cover 520 may be connected to an electrode 550, which in turn may be connected to a power source 560. In addition, the current conducting element 545 disposed on the inner membrane 530 may be connected to a different electrode 550, which in turn may be connected to a different power source 560. A single current may flow through both coils, however, the current may flow in opposite directions in each of the current conducting elements 545 disposed on the inner membrane 530 and the outer cover 520 to cause attractive or repulsive forces between the current conducting elements 545 disposed on the inner membrane 530 and the outer cover 520. For example, the current in the current conducting element 545 disposed on the inner membrane 530 may be counter rotating to the current conducting element 545 disposed on the outer cover 520 so that an opposing magnetic field is generated. This may in turn relax or contract the inner membrane 530.

The contracted state of the inner membrane 530 may allow air to leave the valve device 500 from the distal end 570, but may reduce or prevent air from entering from the proximal end 580. In this manner, inhaled air may be reduced or prevented from entering a portion of the lungs or other organ where the valve device 500 is placed.

As shown in FIGS. 5A and 5B, power, may be provided via electrodes 550 to the actuation components 540. The power may be of any suitable types including, but not limited to, AC/DC electrical power generated by any suitable means.

For example, multiple valve devices may share a combined electrical source, such as a combined inductive coil for their energy supply. The electrical source may be part of an electric circuit to distribute power among multiple valves. The electric circuit may include a bridge rectifier having a receiving portion connected to the power source, such as the pickup portion of an inductive coil. The bridge rectifier may transform the AC signal from the power source, for example from inductive coils, into a DC signal. For example, the distance between two inductive coils, one that may be internal to the body and the other that may be external to the body) that comprise a combined inductive coil power source may change due to movement. This change in distance may impact the height of the AC and thus the DC voltage. In order to alleviate this impact, the voltage may be rectified. For example, the circuit may include a precision voltage rectifier. In such a precision voltage rectifier, when the input voltage is negative, no current may flow through the load, and the output voltage may be zero. When the input is positive, it may be amplified by an operational amplifier and current may then flow through the load and, because of the feedback, the output voltage may be equal to the input voltage, and thereby rectified.

Once a constant DC voltage supply is established, for example, using the precision voltage rectifier described above, the circuit may include voltage distribution components to distribute power to the multiple valves. For example, a flip-flop circuit component which may switch between two stable states and can be used to store state information. Such a flip-flop switch may include a D-type flip-flop, which may change output on the rising edge of a clock signal that oscillates between a high and a low state.

The two outputs Q and not-Q of the flip-flop may be connected to two operational amplifiers (Op-Amps), which may produce an output voltage that may be larger than the voltage difference between the input terminals. The Op-Amps may be connected to the outputs (Q and not-Q) of the flip-flop in non-inverting voltage following configuration connected directly to the valves. The flip-flop may involve changing the output on the clock signal which may be linked to the detected breathing frequency via an input, such as an RF input. To transfer the clock signal to the input of the flip-flop, a RF transmitter may be used to separate from the inductive circuit as the energy requirement may be low. In addition, the circuit may include a microcontroller directly after the voltage rectifier, which may switch the current between multiple valve devices with programmable relaxed/contracted times for each valve device. The microcontroller may control overlapping relaxed/contracted times for each valve device and may include algorithms which may allow relaxed/contracted times for each valve to be adjusted as a function of an observed effect. For example, some healthier sections of may be used more than less healthier sections of the lung. Therefore, the microcontroller may adjust the relaxed/contracted times such that the valve device(s) in the certain sections of the lungs remain relaxed at relatively longer time periods than valve device(s) in other sections of the lungs.

Figure 6:
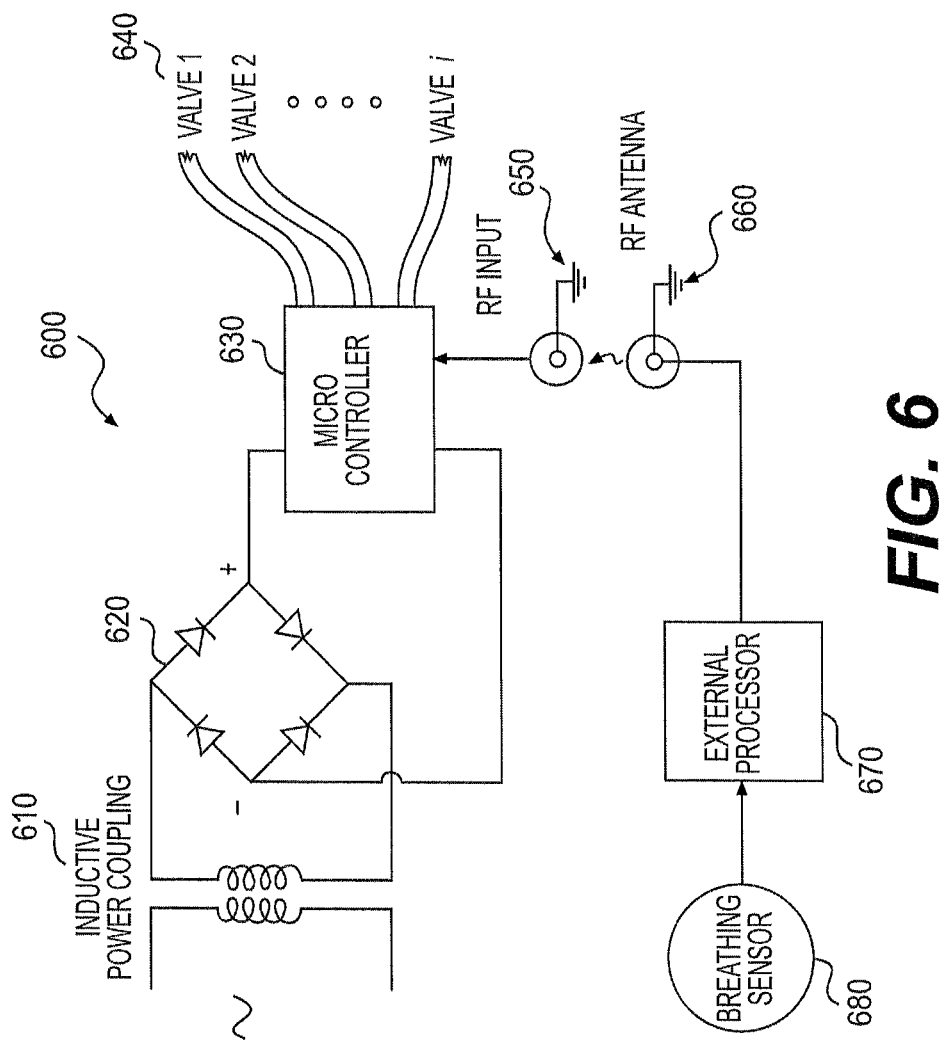
FIG. 6 illustrates an exemplary circuit diagram for controlling valve devices, according to an embodiment of the present disclosure.

In an exemplary embodiment, as illustrated in FIG. 6, multiple valve devices 640 may share a combined electrical power source, for example, an inductive coil 610 for their energy supply in a circuit system 600.

In an embodiment, the inductive coils 610 may act as an electrical transformer to produce high-voltage pulses from a low-voltage direct current (DC) supply. The inductive coils 610 may be connected to a bridge rectifier 620 which may transform the AC signal out of the coils 610 into a DC signal. The rectifier 620 may rectify any changes in voltage due to movement which may alter the distance between the two inductive coils 610 (external and internal to the body). The voltage then may be distributed to the various valve devices 640, for example, using a delayed (D-type) flip-flop (or multi-stable vibrator configuration), which may change output on the rising edge of a clock signal that oscillates between a high and a low state.

The two outputs Q and not-Q of the flip-flop may be connected to two Op-Amps in non-inverting voltage following configuration connected directly to the valves 640. The flip-flop may involve changing output on the clock signal which may be linked to the breathing frequency via an input, such as an RF input 650.

The breathing frequency or breathing cycle may be detected by a breathing sensor 680 connected to an external processor 670 and the breathing frequency may in turn be transmitted by a transmitter, for example, an RF antenna 660 to the receiver, e.g. RF input 650 connected to the microcontroller 630.

The breathing sensor 680 may be one similar to disclosed by Marani, R, et al., *A New System for Continuous Monitoring of Breathing and Kinetic Activity Journal of Sensors*, Volume 2010, Article ID 43486, which includes an electrical conductive rubber belt, worn around the thorax. Using this configuration, breathing cycles may be identified. To transfer the clock signal to the input of the flip-flop, a RF transmitter may be used that is separate from the inductive circuit 600.

The microcontroller 630 may be placed directly after the voltage rectifier 620 for switching the current between multiple valves 640 with programmable relaxed/contracted times of each valve 640. The microcontroller 630 may be able to overlap between the valves 640, and may include algorithms allowing the relaxing and contracted times to be adjusted as a function of the effect seen from sensing the breathing cycle of a patient. Accordingly, actuation components (like 540) of one or more valve devices 500 may be switched between actuated and non-actuated states by controlling the frequency of power supplied to the actuation components. For example, the frequency of actuation of the actuation components 540 of the valve devices 500 may be controlled by the microcontroller 630 based on the breathing cycle of a patient as detected by the breathing sensor 680 and transmitted to the microcontroller 630 by the RF antenna 660 via the RF input 650.

In another embodiment, the power supply to the valves may be stored at the valves itself using thin film capacitors charged by low power RF energy. For example, if the valves are used periodically, the capacitors may be charged during the long intermediate time-frames. For instance, the capacitors may be used to power valve devices used to block cigarette smoke from entering portions of the lungs. In this example, the capacitors are charged when the valves are not in use (e.g. when the patient is not smoking). Any suitable source of RF energy may be used, for example, Wi-Fi and other mobile base stations and handsets and devices may be used. In addition, RF may be broadcasted from other sources in unlicensed bands such as 868 MHz, 915 MHz, 2.4 GHz, and 5.8 GHz when more power or more predictable energy is needed than what is available from ambient sources. In another example, the same RF system may be used to switch the valve device, by signaling a built in microprocessor to utilize the stored energy to close the valve. A return signal can be given to the user that the valves are closed and one can start smoking.

Figure 7:
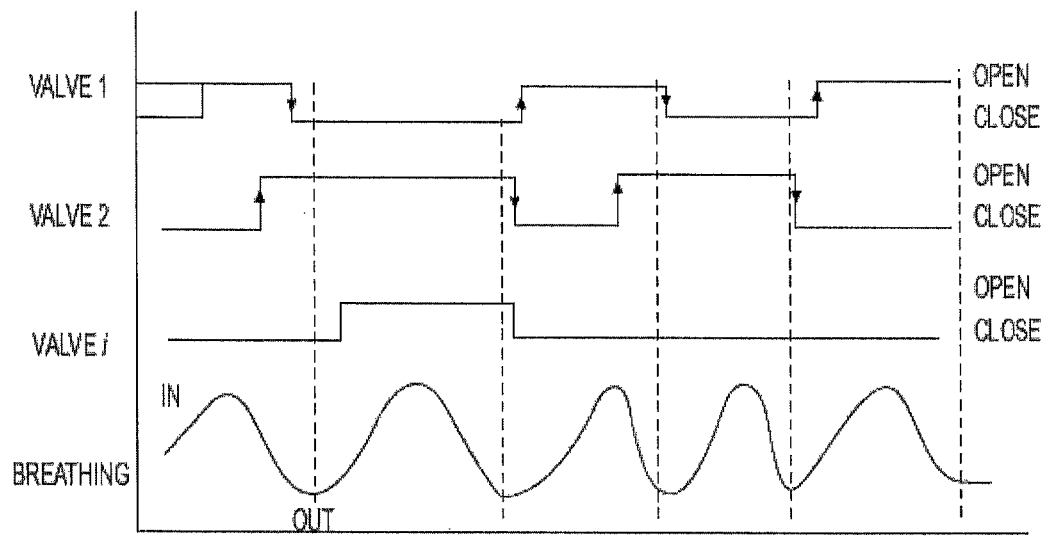
FIG. 7 is a graph showing relaxed and closed positions of valve devices synchronized with inhalation frequency, according to an embodiment of the present disclosure.

FIG. 7 shows an example of relaxed and contracted times of various valves as a function of a breathing cycle. In this example, some sections of the lung which are less affected by COPD may be used more than severely affected. As such valves 1 and 2 which may be in healthier lobes of the lung have longer relaxed times compared to valve "I" in an affected lobe of the lung. These relaxed and contracted times as controlled by the microcontroller may be adjusted based on the breathing cycle.

The above discussed valve devices may also be used to prevent exposure of parts of the lungs to cigarette smoke, especially for patients with a severe stage of COPD including patients with emphysema.

Figure 8:
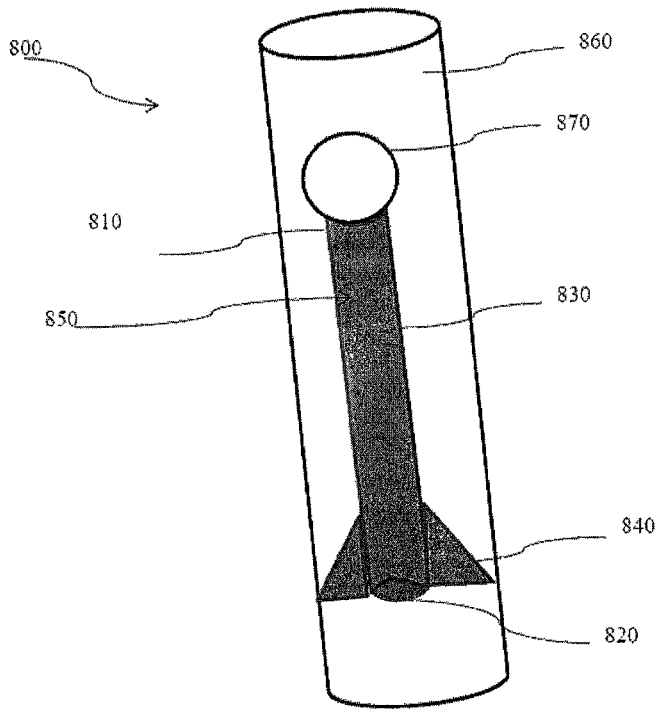
FIG. 8 illustrates a flow control device according to another embodiment of the present disclosure.

In another exemplary embodiment, as shown in FIG. 8, a tube device 800 having a proximal end 810 that may be disposed in or adjacent a tracheostomy orifice and a distal end 820. A tubular member 830 having a lumen 850 may extend between the proximal end 810 and distal end 820. The tubular member 830 and lumen 850 may have any suitable shape, diameter and/or size, which may vary along the length of the tube device 800. The tubular member 830 may include a coating on all or a portion that may have lubricious, therapeutic and/or porous properties.

The distal end may include an expandable component 840, that may be expanded via any suitable means, including, but not limited to electro-active (EAP) polymer actuation, pneumatic actuation (e.g., compressed air/gas such as a balloon), electrical actuation, hydraulic actuation, piezoelectric actuation, thermal actuation, electrostatic actuation, magnetic actuation, inductive actuation, the body's own forces, and any other suitable actuation methods. The expandable component 840 may take any suitable shape or geometry, including an annular shape as shown in FIG. 8. The material of the expandable component may be any suitable material including polytetrafluoroethylene (PTFE), polyethylene, FEP (fluorinated ethylene propylene), ETFE (ethylene tetrofluoroethylene), polypropylene, polysulfone, polyethylene, polyethersulfone, silicone, silicon rubber, etc. The expandable component 840 may include a coating that may have lubricious, therapeutic and/or porous properties.

The expandable member 840 may be inflated to seal the bronchus so that only air entering from the tracheostomy may enter the lung. In this manner, if it is determined that one lung has less disease than the other, then the healthy lung may be isolated so that it may not be exposed to further smoke and subsequently may slow the rate of decline of lung function in that lung and oxygen therapy may be administered directly. The tube device 800 may be used to prevent smoke from enter the lung while allowing air from the trachea opening to enter the lung.

One or more of the tubular member 800 and/or any of the valve devices, and any combination thereof disclosed herein may be placed in the body, such as in the second or third bifurcation of the trachea. The tube device 800 and/or the valve devices may be expanded (in the case of the tubular member 800)/contracted (in the case of the valve devices) by the patient using an RF system as describe above. The tube device 800 and/or the valve devices may normally be in the non-expanded/relaxed state, but may be temporarily switched to the expanded/contracted state upon actuation. The power supply for the tube device 800 and/or valve devices may be stored at the device itself using thin filmcapacitors charged by low power RF energy as described above.

Embodiments of the present disclosure may be used in any medical or non-medical procedure, including any medical procedure where control of air into and out of the lungs is desired. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A device for selectively controlling air flow in a patient, the device comprising:
   a member having a proximal end, a distal end, and a lumen extending therebetween;
   an inner member disposed about a portion of the lumen, wherein the inner member is configured to transition between a first configuration and a second configuration, wherein, in the first configuration, the portion of the lumen including the inner member defines a first diameter, and, in the second configuration, the portion of the lumen including the inner member defines a second diameter smaller than the first diameter;
   an actuation member for transitioning the inner member between the first configuration and the second configuration; and
   a controller configured to send an output to the actuation member, the controller being configured to:
      increase a rate at which the inner member transitions between the first configuration and the second configuration when a frequency of inhalation and exhalation of a lung of the patient increases; and
      decrease the rate at which the inner member transitions between the first configuration and the second configuration when the frequency of inhalation and exhalation in the lung decreases.

2. The device of claim 1, wherein the member comprises a wire frame having a plurality of interconnected wires, and the wire frame comprises an outer cover disposed about a portion of the wire frame.

3. The device of claim 1, wherein the actuation member is configured to transition the inner member from the first configuration to the second configuration in response to a magnetic force.

4. The device of claim 1, wherein the actuation member includes an electro-active polymer disposed on the inner member, and the electro-active polymer is connected to an electrical power source.

5. The device of claim 1, wherein the actuation member is configured to transition the inner member from the first configuration to the second configuration in response to a stimulus, and the inner member is biased in one of the first or second configurations.

6. The device of claim 1, further including a breathing sensor operatively coupled to the controller, the breathing sensor including an electrically conductive element, wherein the breathing sensor is configured to detect the frequency of inhalation and exhalation of the lung.

7. The device of claim 6, wherein the breathing sensor is configured to detect the frequency of inhalation and exhalation of the lung while coupled to a thorax.

8. A system for controlling air flow in parts of a lung, the system comprising:
 a plurality of valve devices; and
 a controller coupled to the plurality of valve devices configured to control energy supplied to the plurality of valve devices,
 wherein each of the plurality of valve devices comprises:
  an elongate member having a proximal end, a distal end, and a lumen extending therebetween,
  an inner member disposed about a portion of the lumen, wherein the inner member is configured to transition between a first configuration and a second configuration, wherein, in the first configuration, the portion of the lumen including the inner member defines a first diameter, and, in the second configuration, the portion of the lumen including the inner member defines a second diameter smaller than the first diameter, and
  an actuation member for transitioning the inner member between the first configuration and the second configuration, wherein the actuation member is disposed on a portion of the inner member, wherein the controller is configured to transition each of the plurality of valve devices between the first configuration and the second configuration based on a detected breathing cycle of the lung, wherein the plurality of valve devices includes a first valve device configured to be placed in a first airway of the lung, and a second valve device configured to be placed in a second airway of the lung that is different than the first airway of the lung, and wherein, over a period of one day, the controller is configured to maintain the first valve device in the first configuration for a higher percentage of time than the second valve device is maintained in the first configuration based on respective locations of the first airway and the second airway in the lung, and based on an ability of the lung to expand in portions adjacent to the first airway and the second airway.

9. The system of claim 8, wherein the elongate member comprises a wire frame.

10. The system of claim 9, wherein the actuation member includes a plurality of magnets.

11. The system of claim 9, wherein the wire frame comprises an outer cover disposed about a portion of the wire frame.

12. The system of claim 8, wherein the actuation member includes an electro-active member disposed on the inner member, and the electro-active member is deposited in one or more vertical stripes.

13. The system of claim 8, wherein the actuation member is configured to transition the inner member from the first configuration to the second configuration, and the inner member is biased in one of the first or second configurations.

14. The system of claim 8, wherein the controller is configured to transition each of the plurality of valve devices between the first configuration and the second configuration by changing a frequency of the energy supplied to the plurality of valve devices.

15. The system of claim 8, further including a breathing sensor operatively coupled to the controller, the breathing sensor including an electrically conductive element, wherein the breathing sensor is configured to detect the breathing cycle of the lung while coupled to a thorax of a patient.

16. The system of claim 15, further including a wireless output operatively coupled to the breathing sensor, and a wireless receiver operatively coupled to the controller, wherein the wireless output is configured to send a wireless signal indicative of the detected breathing cycle to the wireless receiver.

17. The system of claim 8, wherein the controller is configured to increase a rate at which at least one of the plurality of valve devices transitions between the first configuration and the second configuration when a rate of inhalation and exhalation increases in the lung.

18. A system for controlling air flow in a lung, the system comprising:
 a first valve device configured to be placed in a first airway of the lung, and a second valve device configured to be placed in a second airway of the lung that is different than the first airway of the lung;
 an energy supply including an inductive coil configured to deliver energy to each of the first valve device and the second valve device;
 a controller coupled to the first valve device and the second valve device, the controller being configured to control the energy delivered to the first valve device and the second valve device by the energy supply;
 a wireless receiver operatively coupled to the controller;
 a breathing sensor including an electrically conductive element, wherein the breathing sensor is configured to detect the breathing cycle of a patient while coupled to a thorax of the patient; and
 a wireless output operatively coupled to the breathing sensor, wherein the wireless output is configured to send a wireless signal indicative of the detected breathing cycle to the wireless receiver;
 wherein the first valve device and the second valve device each includes:
  a member having a proximal end, a distal end, and a lumen extending therebetween,
  an inner member disposed about a portion of the lumen, wherein the inner member is configured to transition between a first configuration and a second configuration, wherein, in the first configuration, the portion of the lumen including the inner member defines a first diameter, and in the second configuration, the portion of the lumen including the inner member defines a second diameter smaller than the first diameter, and
  an actuation member for transitioning the inner member between the first configuration and the second configuration, wherein the actuation member is disposed on a portion of the inner member, wherein the controller is configured to transition each of the first valve device and the second valve device between the first configuration and the second configuration based on the detected breathing cycle by changing a frequency of the energy delivered from the energy supply to the first valve device and the second valve device.

19. The system of claim 18, wherein, over a period of one day, the controller is configured to maintain the first valve device in the first configuration for a higher percentage of time than the second valve device is maintained in the first configuration based on respective locations of the first airway and the second airway in the lung, and based on an ability of the lung to expand in portions adjacent to the first airway and the second airway, and the controller is configured to increase a rate at which at least one of the first valve device and the second valve device transitions between the first configuration and the second configuration when a rate of inhalation and exhalation increases in the lung.

\* \* \* \* \*